United States Patent
Tomalinas

(10) Patent No.: US 12,396,754 B2
(45) Date of Patent: Aug. 26, 2025

(54) TICK REMOVAL AND ENCAPSULATION DEVICE

(71) Applicant: William Tomalinas, Mountain Top, PA (US)

(72) Inventor: William Tomalinas, Mountain Top, PA (US)

( * ) Notice: Subject to any disclaimer, the term of this patent is extended or adjusted under 35 U.S.C. 154(b) by 269 days.

(21) Appl. No.: 18/321,519

(22) Filed: May 22, 2023

(65) Prior Publication Data

US 2024/0390035 A1    Nov. 28, 2024

(51) Int. Cl.
*A61B 17/50*    (2006.01)

(52) U.S. Cl.
CPC ........ *A61B 17/50* (2013.01); *A61B 2017/505* (2013.01)

(58) Field of Classification Search
CPC .......................... A61B 17/50; A61B 2017/505
See application file for complete search history.

(56) References Cited

U.S. PATENT DOCUMENTS

| | | | |
|---|---|---|---|
| 2,431,922 A * | 12/1947 | Curtiss | B25C 11/02 30/1.5 |
| 5,116,347 A | 5/1992 | Butler | |
| 5,246,449 A * | 9/1993 | Webster | A61B 17/50 606/1 |
| 5,380,339 A | 1/1995 | Webster | |
| 5,554,161 A | 9/1996 | Thibeault | |
| 5,607,434 A | 3/1997 | Alvino | |
| D388,859 S * | 1/1998 | Carroll, Jr. | D22/122 |
| D889,646 S | 7/2020 | Bauer | |
| 10,980,572 B1 | 4/2021 | Poremba | |
| 11,154,328 B1 | 10/2021 | Gelardi, Sr. | |
| 2006/0271069 A1 | 11/2006 | Glaesel | |
| 2018/0177527 A1 | 6/2018 | Cohen et al. | |

FOREIGN PATENT DOCUMENTS

| | | |
|---|---|---|
| DE | 202014006075 U1 | 11/2014 |
| DE | 102016113582 A1 | 1/2018 |
| ES | 2347712 | 11/2010 |
| ES | 2657196 | 3/2018 |

* cited by examiner

*Primary Examiner* — Anh T Dang
(74) *Attorney, Agent, or Firm* — Michael J. Feigin, Esq.; Feigin and Fridman LLC

(57) ABSTRACT

A tick removal and capturing device of embodiments of the disclosed technology includes a first end and a second end removably attachable to the first end, with a pivot point attached there-between. A removably attached combination of the first and second ends form a tick removal head and a tick encapsulation chamber, the chamber disposed between the tick removal head and the pivot point. The tick encapsulation chamber is adapted to substantially fully encapsulate a tick therein in the removably attached combination.

19 Claims, 3 Drawing Sheets

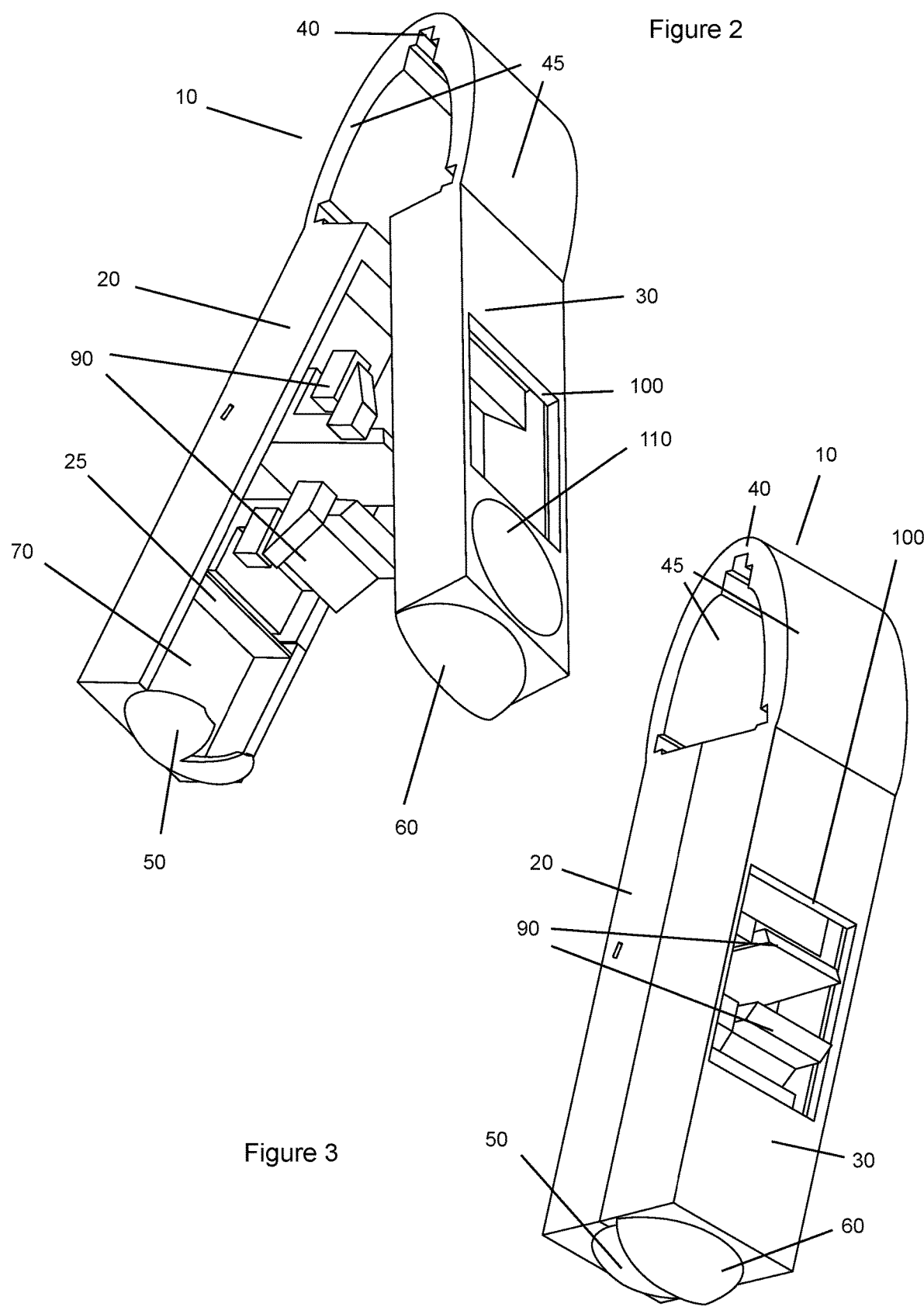

TICK REMOVAL AND ENCAPSULATION DEVICE

FIELD OF THE DISCLOSED TECHNOLOGY

The disclosed technology relates generally to tick removal devices, and more specifically to a device for simultaneously removing a tick from a surface and securing the tick for further analysis.

BACKGROUND OF THE DISCLOSED TECHNOLOGY

Lyme disease is a disease which infects many people yearly. This disease is often contracted by way of bites from infected ticks incurred while spending time outdoors. When ticks are found after time outdoors, it is necessary to find a way to remove them properly, and occasionally test them, to prevent or diagnose potential tick borne diseases such as Lyme disease. However, properly removing and sending ticks for testing can be difficult, as portions of the tick can occasionally be removed from the tick's body and left in the human host's body during removal. There is therefore a need for a device to allow for safe removal of ticks and encapsulation of removed ticks in order to prevent disease and/or send ticks for disease testing after removal.

SUMMARY OF THE DISCLOSED TECHNOLOGY

A tick removal and capturing device of embodiments of the disclosed technology includes a first linear portion in a shape of a rectangular prism and a second linear portion, removably attachable along a longest linear extent thereof to a longest linear extent of the first linear portion, in a shape of a rectangular prism. The first and second linear portions each have a first end and a second end. A U-shaped pivot point is attached to the second ends of both the first and the second linear portions, with a thinnest portion at a center thereof.

The first ends of the first and second linear portions of embodiments of the disclosed technology are a tick remover head. The first end of the first liner portion is a concave semi-circle. The first end of the second linear portion is a majority of a concave circle. "Concave circle" and "concave semi-circle" are defined, respectively, as a circle or a semi-circle which is curved such that a distance of a central point of a circle thereof from the pivot point is greater than a distance from the pivot point to edges of the circle.

In embodiments, in an arrangement where the first and second linear portions are removably attached along longest linear extents thereof, a hollow within the first linear portion and a corresponding hollow within the second linear portion reversibly form a tick encapsulation chamber.

When joined, the first and second linear portions may form a rectangular prism.

In the removably attached configuration, in various embodiments, the tick remover head forms a side of the tick encapsulation chamber. Furthermore, in the removably attached configuration, the tick remover head is covered by a head cover, which substantially forms a seal over a seam between the first end of the first linear portion and the first end of the second linear portion.

The sides of the pivot, in embodiments, are rotatable by way of a pivot point up to an angle of substantially 180 degrees.

In the arrangement where the first and second linear portions are removably attached along longest linear extents thereof, the second linear portion may further have at least one deformable protrusion adapted to prevent detachment of the first and second linear portions along longest linear extents thereof unless acted upon by an external force substantially greater than a normal force thereof and/or a force due to gravity.

The at least one deformable protrusion may further be adapted, when the first and second linear portions are detached along a longest linear extent of each of the first and the second linear portions, to prevent attachment of the first and second linear portions along longest linear extents thereof unless acted upon by an external force substantially greater than a normal force thereof and/or a force due to gravity.

In some embodiments, at least one of the first and second linear portions further comprise a second pivot point between extreme ends thereof, being a pivot point between the first end of the at least one linear portion away from the other linear portion.

The tick encapsulation chamber may encapsulate a tick therein in the arrangement where the first and second linear portions are removably attached along longest linear extents thereof. "Encapsulate" is defined as enclosing an object therein in a structure such that the object cannot be removed from the structure without substantially deforming the object or the structure.

Described differently, a tick removal and capturing device has a first end, a second end removably attachable to the first end, and pivot point there-between. A removably attached combination of the first end and the second end forms a tick removal head and a tick encapsulation chamber, the chamber disposed between the head and the pivot point and adapted to substantially fully encapsulate a tick therein in the removably attached combination.

In the removably attached combination, the tick removal head may form a wall of the tick encapsulation chamber.

The tick removal head may include at least one element disposed on the first end and at least one element disposed on the second end. In the removably attached combination, the tick removal head may be covered by a head cover, which may substantially form a seal over a seam between edges of the at least one element of the tick removal head disposed on the first end and the at least one element of the tick removal head disposed on the second end.

The first end may be rotatable by way of the pivot point substantially up to 180 degrees relative to the second end.

At least one of the ends may include at least one deformable protrusion adapted, in an arrangement where the first and second ends are reversibly combined, to substantially prevent reversion of the combination unless acted upon by an external force substantially greater than a normal force thereof and/or a force due to gravity. Furthermore, the at least one deformable protrusion may be adapted, in an arrangement where the first and second ends are reversibly disconnectable, to substantially prevent combination of the first and second ends unless acted upon by an external force substantially greater than a normal force thereof and/or a force due to gravity.

In some embodiments, at least one end of the first and second ends further includes a second pivot point between extreme ends thereof, being a pivot point between an extreme end of the at least one end away from an other of the first and second ends.

A method of used the aforementioned tick removal and capturing device includes steps of removably combining the first and second ends such that a tick is encapsulated in the tick encapsulation chamber, and removably separating the first and second ends such that the tick is removable from the tick encapsulation chamber.

In some embodiments, the step of removably combining the first and second ends such that a tick is encapsulated in the tick encapsulation chamber is preceded by a step of using the tick remover head to remove a tick from a surface external to the device such that the tick is placed within a portion of the tick encapsulation chamber.

In other embodiments of the disclosed technology, the step of removably combining the first and second ends such that a tick is encapsulated in the tick encapsulation chamber is simultaneously a step of using the tick remover head to remove a tick from a surface external to the device such that the tick is placed within a portion of the tick encapsulation chamber.

In further embodiments, the step of using the tick remover head to remove a tick from a surface external to the device such that the tick is placed within a portion of the tick encapsulation chamber is preceded by a step of changing an angle between the first and second ends of the device by way of the pivot point such that the a location of the tick on the surface external to the device is accessible to the tick remover head.

Any device or step to a method described in this disclosure can comprise or consist of that which it is a part of, or the parts which make up the device or step. The term "and/or" is inclusive of the items which it joins linguistically and each item by itself.

BRIEF DESCRIPTION OF THE DRAWINGS

FIG. 2 shows a bottom and left perspective view of the tick removal device in the open configuration of FIG. 1.

FIG. 3 shows a bottom and left perspective view of a tick removal device in a closed configuration of embodiments of the disclosed technology.

DETAILED DESCRIPTION OF EMBODIMENTS OF THE DISCLOSED TECHNOLOGY

A tick removal and capturing device of embodiments of the disclosed technology includes a first end and a second end removably attachable to the first end, with a pivot point attached there-between. A removably attached combination of the first and second ends form a tick removal head and a tick encapsulation chamber, the chamber disposed between the tick removal head and the pivot point. The tick encapsulation chamber is adapted to substantially fully encapsulate a tick therein in the removably attached combination.

Embodiments of the disclosed technology will become more clear in view of the following discussion of the figures.

Figure 1:
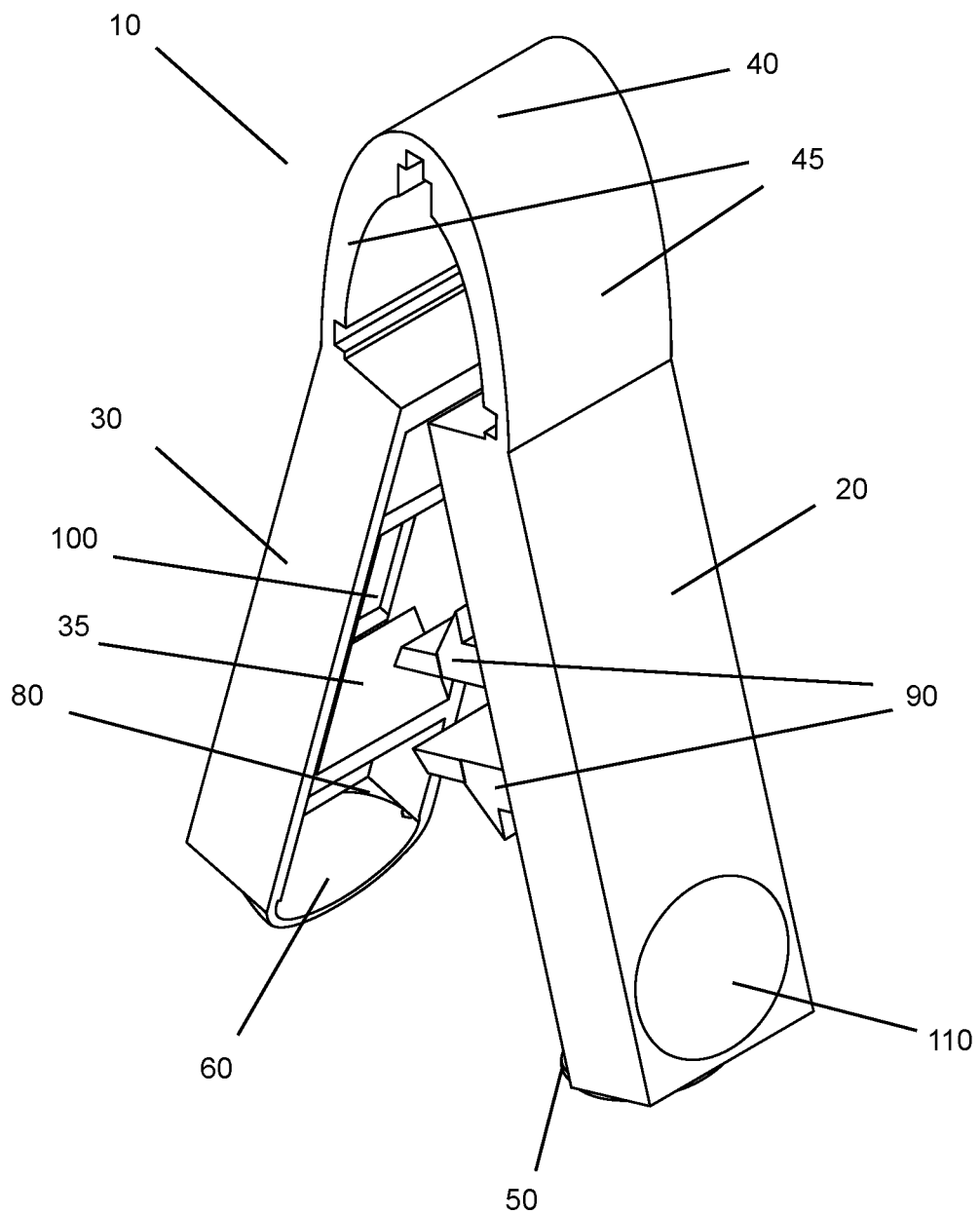
FIG. 1 shows a top and right perspective view of a tick removal device in an open configuration of embodiments of the disclosed technology.

FIG. 1 shows a top and right perspective view of a tick removal device in an open configuration of embodiments of the disclosed technology. FIG. 2 shows a bottom and left perspective view of the tick removal device in the open configuration of FIG. 1. The device 10 has a first side 20 and a second side 30, which are substantially same lengths, widths, and shapes. The first side 20 ends in a first end 50, and the second side 30 ends in a second end 60.

The two sides 20, 30 are connected by a pivot 40. In the embodiment shown, the pivot 40 has two arms 45, each of which is connected to an end of the sides 20, 30 which is opposite the first and second ends 50, 60. In some embodiments, the pivot 40 further includes additional pivot points between the pivot 40 and the first and second sides 20, 30. In other embodiments, the pivot 40 may be any other form of pivot joint between the two sides 20, 30 that restricts rotation of the two sides 20, 30 there-about to being in a single plane.

In the embodiment shown, the first side 20 includes a pair of rigid deformable structures 90. A "rigid deformable structure" is defined as a structure whose exterior shape can be temporarily changed by way of pressure applied by two fingers of an average human" such as 50 Newtons. The second side 30 includes a portal 100 corresponding to the locations of the rigid deformable structures 90. In various embodiments, the rigidly deformable structures 90 may be only a single structure 90 or may be any number of structures 90. The portal 100 may be any number of portals, such that each rigid deformable structure 90 corresponds to at least one portal 100. In various embodiments, the portal 100 may be on the first side 20 and the rigid deformable structures 90 may be on the second side 30.

The two sides 20, 30, in the embodiment shown, include a plurality of grips 110 at ends thereof near the first and second ends 50, 60. The grips, in the embodiment shown, are convex in shape, where "convex" is defined as being curved such that a width of a surface in which a convex shape is disposed is wider at edges thereof than at a most convex point thereof, such that the surface is deeper at the most convex point thereof. In other embodiments, the grips may be any other shape, or made of may other material, or placed in any location such that a finger may be inserted therein and exert sufficient force to operate the device 10 while remaining substantially stationary due to at least a normal force and a force of friction and not interfering with operation of the device 10.

The first side 20 includes a first hollow 70, having a single portal, and the second side 30 includes a second hollow 80, having a single portal. The hollows 70, 80 and the portals thereof are aligned, such that when the two sides 20, 30 are brought into contact by way of rotation about the pivot 40, the hollows 70, 80 form a single enclosure substantially lacking any external portals. In various other embodiments, the single enclosure may be of any shape and may comprise holes of a size such that an average-size adult or non-larvae tick is unable to pass there-through while remaining structurally intact, such as half a millimeter. In some embodiments, one of the sides 20, 30 may include a hollow 70, 80 while the other side 20, 30 includes a corresponding cover, such that the hollow 70 or 80, when covered by the corresponding cover, forms a single enclosure substantially lacking any external portals.

In the embodiment shown, the first hollow 70 has a wall 25 between the hollow 70 and the rigid deformable structures 90 and the second hollow 80 has a wall 35 between the hollow 80 and the portal 100.

In embodiments, one or more of the grips 110 are located on a portion of the sides 20, 30 corresponding to the internal hollows 70, 80 thereof. In some embodiments where one or more of the grips 110 are in forms of convex circles, a most convex point of one or more of the grips 110 bulges into the internal hollows 70, 80. In other embodiments, a surface between the hollows 70, 80 and the grip or grips 110 is substantially flat on a side which is internal to the hollows 70, 80 and is thinnest at a point thereof corresponding to the most convex point of one or more of the grips 110.

In the embodiment shown, the first end 50 is a tick remover and the second end 60 is a tick remover cover. In other embodiments, the two ends 50, 60 may form a single tick remover, or each may be a tick remover, and the tick remover cover may be a separate removably attachable component. In the embodiment shown, the first end 50 is in a shape of a concave circle lacking a minority segment including a hollow point. The second end 60 is in a shape of a concave semicircle. The concave circle lacking a minority segment is disposed on the first end 50 such that an intact half thereof is attached to the first end 50, and the concave semicircle is disposed substantially entirely on the second end 60 with a linear portion thereof facing the lacking minority segment of the concave circle on the first end 50. In the embodiment shown, each of the circle attached to the first end 50 and the semicircle attached to the second end 60 simultaneously forms a wall of the hollow 70, 80 of their corresponding sides 20, 30.

FIG. 3 shows a bottom and left perspective view of a tick removal device in a closed configuration of embodiments of the disclosed technology. In the closed configuration shown, the sides 20, 30 are brought flush against each other by way of rotation about the pivot 40 and the rigid deformable structures 90 are or have been deformed such that portions thereof pass through the portal 100.

The pivot 40 may tend to a single position, such as a single angle between the sides 20, 30, such that while deformed into a different position, such as a different angle between the sides 20, 30, the pivot 40 pushes the sides 20, 30 back into the preferred position unless the sides 20, 30 are held in place by an external force. Thus, in some embodiments, while in the closed configuration as shown, the sides 20, 30 may be pressed outward, toward a larger angle there-between, such that portions of the rigid deformable structures 90 are pressed against portions of an edge of the portal 100. In such embodiments, the device 10 may be returned to the preferred position by way of deforming the rigid deformable structures 90 such that they may fully pass through the portal 100 simultaneously.

In the closed configuration shown, a seam between the two sides 20, 30 may be substantially flush, such that substantially no portal exists there-between, at least at portions thereof surrounding the internal combined hollows 70, 80. Furthermore, the tick cover, such that the concave semi-circle attached to the second end 60, may be substantially fully flush with solid portions of the tick remover at the first end 50, such that substantially no portals exist in the combination of the first and second ends 50, 60 while in the closed configuration. Additionally, the walls 25, 35 of the hollows 70, 80 may be substantially flush, such that no portals exist in the combination thereof.

Figure 4:
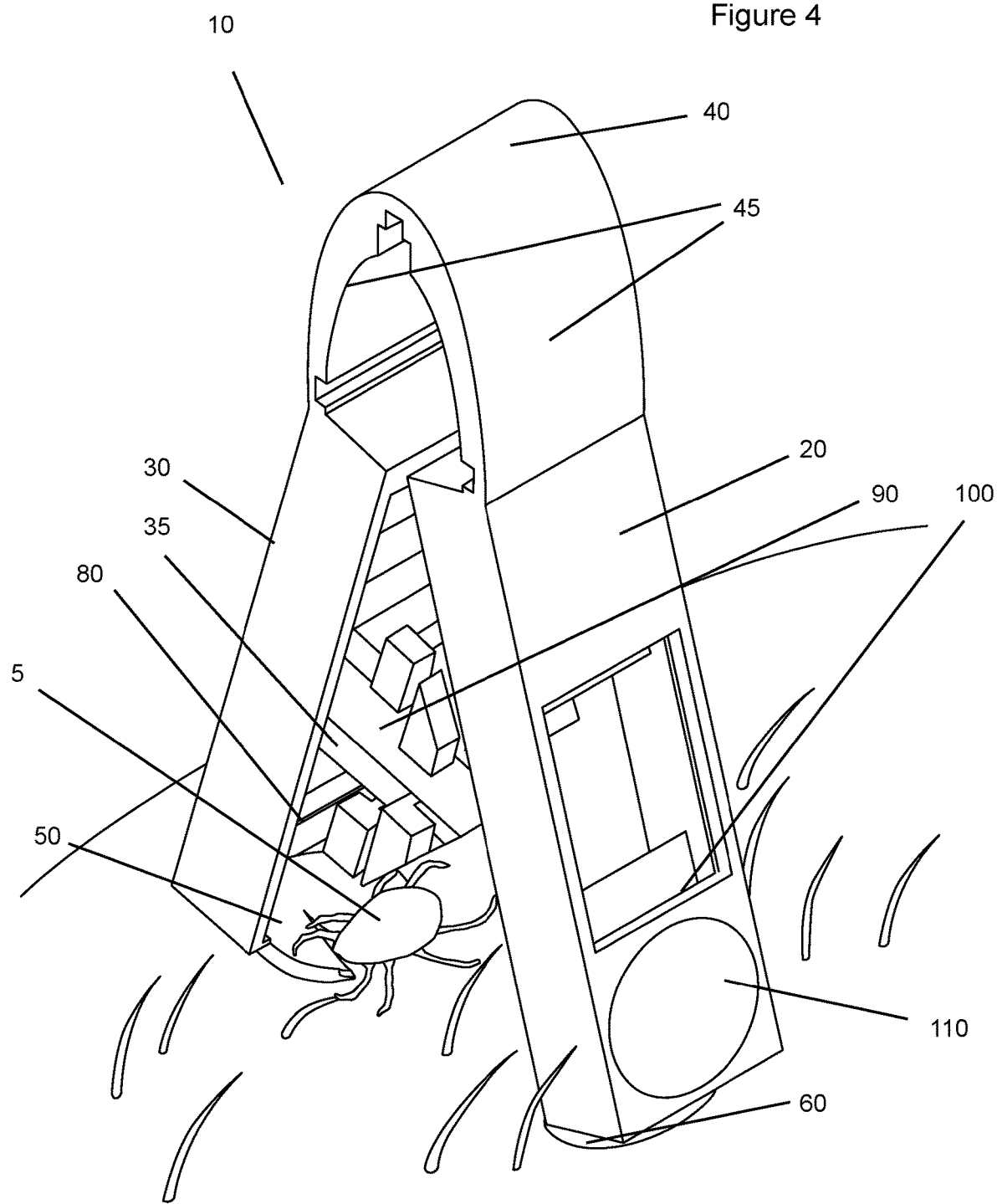
FIG. 4 shows a top and right perspective view of the tick removal device in the open configuration of FIG. 1.

FIG. 4 shows a top and right perspective view of the tick removal device in the open configuration of FIG. 1. The tick remover at the first end 50, in the embodiment shown, is sized to remove a tick 5 from a surface, such as skin, while keeping the tick 5 intact. The sides 20, 30 may be rotated together such that the tick is removed while the rigid deformable structures 90 are deformed, such as by pressing against angled portions within the device 10. Thus, the tick 5 may be simultaneously removed by way of the tick remover at the first end 50 and placed into the first hollow 70 while the first and second ends 20, 30 are rotated into the closed configuration such that the internal hollow is formed by way of combination of the first hollow 70, second hollow 80, first and second ends 50, 60 and walls 25, 35, substantially enclosing the tick 5 therein.

In embodiments, the sides 20, 30 may be rotated about the pivot 40 such that an angle there-between is increased relative to the preferred angle. The pivot 40 may furthermore be constructed such that the angle there-between is limited to a maximal angle, such as 180 degrees, while being rotated by use of normal human force while using the device 10.

In further embodiments, one or more of the sides 20, 30 may further include one or more internal pivots therein, such that a corresponding end 50, 60 may be rotated farther from the opposite end 20, 30. In such embodiments, one or more of the sides 20, 30 may include further locking mechanisms, such as further rigid deformable structures, such that the sides 20, 30 are lockable in an unbent shape.

For purposes of this disclosure, the term "substantially" is defined as "between 95% and 100%, inclusive, of" the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been disclosed with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. A tick removal and capturing device, comprising:
  a first linear portion in a shape of a rectangular prism comprising a first end and a second end;
  a second linear portion, removably attachable along a longest linear extent thereof to a longest linear extent of said first linear portion, in a shape of a rectangular prism comprising a first end and a second end; and
  a U-shaped pivot point attached to said second ends of said first and said second linear portions comprising a thinnest portion at a center thereof;
  wherein said first ends of said first and second linear portions comprise a tick remover head;
  wherein said first end of said first linear portion comprises a concave semi-circle; wherein said first end of said second linear portion comprises a majority of a concave circle;
  wherein in an arrangement where said first and second linear portions are removably attached along longest linear extents thereof, a hollow within said first linear portion and a corresponding hollow within said second linear portion reversibly form a tick encapsulation chamber;
  wherein, in said removably attached configuration, said tick remover head is covered by a head cover, said head cover substantially forming a seal over a seam between said first end of said first linear portion and said first end of said second linear portion.

2. The tick removal and capturing device of claim 1, wherein said first and said second linear portions, when joined, form a rectangular prism.

3. The tick removal and capturing device of claim 1, wherein, in said removably attached configuration, said tick remover head forms a side of said tick encapsulation chamber.

4. The tick removal and capturing device of claim 1, wherein sides of said pivot point are rotatable by way of a pivot point up to an angle of substantially 180 degrees.

5. The tick removal and capturing device of claim 1, wherein said second linear portion further comprises at least one deformable protrusion adapted, in said arrangement where said first and said second linear portions are removably attached along longest linear extents thereof, preventing detachment of said first and said second linear portions along longest linear extents thereof unless acted upon by an external force substantially greater than a normal force thereof and/or a force due to gravity.

6. The tick removal and capturing device of claim 1, wherein said second linear portion further comprises at least one deformable protrusion, wherein said first and said second linear portions are detached along a longest linear extent of each said first and said second linear portions, preventing attachment of said first and said second linear portions along longest linear extents thereof unless acted upon by an external force substantially greater than a normal force thereof and/or a force due to gravity.

7. The tick removal and capturing device of claim 1, wherein at least one of said first and second linear portions further comprises a second pivot point between extreme ends thereof, being a pivot point between said first end of said at least one linear portion away from said other linear portion.

8. The tick removal and capturing device of claim 1, wherein said tick encapsulation chamber encapsulates a tick therein in said arrangement where said first and second linear portions are removably attached along longest linear extents thereof.

9. A tick removal and capturing device, comprising:
a first linear portion in a shape of a rectangular prism comprising a first end and a second end;
a second linear portion, removably attachable along a longest linear extent thereof to a longest linear extent of said first linear portion, in a shape of a rectangular prism comprising a first end and a second end; and
a U-shaped pivot point attached to said second ends of said first and said second linear portions comprising a thinnest portion at a center thereof;
wherein said first ends of said first and second linear portions comprise a tick remover head;
wherein said first end of said first linear portion comprises a concave semi-circle; wherein said first end of said second linear portion comprises a majority of a concave circle;
wherein in an arrangement where said first and second linear portions are removably attached along longest linear extents thereof, a hollow within said first linear portion and a corresponding hollow within said second linear portion reversibly form a tick encapsulation chamber;
wherein at least one of said first and second linear portions further comprises a second pivot point between extreme ends thereof, being a pivot point between said first end of said at least one linear portion away from said other linear portion.

10. A tick removal and capturing device, comprising:
a first linear portion in a shape of a rectangular prism comprising a first end;
a second linear portion in a shape of a rectangular prism comprising a second end removably attachable to said first end; and
a pivot point between said first and said second ends;
wherein a removably attached combination of said first end and said second end forms a tick removal head and a tick encapsulation chamber, said chamber disposed between said tick removal head and said pivot point and adapted to substantially fully encapsulate a tick therein in said removably attached combination;
wherein said tick removal head comprises at least one element disposed on said first end and at least one element disposed on said second end;
wherein in said removably attached combination said tick removal head is covered by a head cover, said head cover substantially forming a seal over a seam between edges of said at least one element of said tick removal head disposed on said first end and said at least one element of said tick removal head disposed on said second end.

11. The tick removal and capturing device of claim 10, wherein in said removably attached combination said tick removal head forms a wall of said tick encapsulation chamber.

12. The tick removal and capturing device of claim 10, wherein said first end is rotatable by way of said pivot point substantially up to 180 degrees relative to said second end.

13. The tick removal and capturing device of claim 10, wherein at least one of said ends comprises at least one deformable protrusion adapted, in an arrangement where said first and second ends are reversibly combined, to substantially prevent disconnection of said combination unless acted upon by an external force substantially greater than a normal force thereof and/or a force due to gravity.

14. The tick removal and capturing device of claim 13, wherein said at least one deformable protrusion is further adapted, in an arrangement where said first and second ends are reversibly disconnectable, to substantially prevent combination of said first and second ends unless acted upon by an external force substantially greater than a normal force thereof and/or a force due to gravity.

15. The tick removal and capturing device of claim 10, wherein at least one end of said first and second ends further comprises a second pivot point between extreme ends thereof, being a pivot point between an extreme end of said at least one end away from an other of said first and second ends.

16. A method of using the tick removal and capturing device of claim 10, comprising steps of:
removably combining said first and second ends such that a tick is encapsulated in said tick encapsulation chamber; and
removably disconnecting said first and second ends such that said tick is removable from said tick encapsulation chamber.

17. The method of using the tick removal and capturing device of claim 16, wherein said step of removably combining said first and second ends such that a tick is encapsulated in said tick encapsulation chamber is preceded by a step of using said tick remover head to remove a tick from a surface external to said device such that said tick is placed within a portion of said tick encapsulation chamber.

18. The method of using the tick removal and capturing device of claim 16, wherein said step of removably combining said first and second ends such that a tick is encapsulated in said tick encapsulation chamber simultaneously comprises a step of using said tick remover head to remove a tick from a surface external to said device such that said tick is placed within a portion of said tick encapsulation chamber.

19. The method of using the tick removal and capturing device of claim 17, wherein said step of using said tick remover head to remove a tick from a surface external to said device such that said tick is placed within a portion of said tick encapsulation chamber is preceded by a step of changing an angle between said first and second ends of said device by way of said pivot point such that said a location of said tick on said surface external to said device is accessible to said tick remover head.

\* \* \* \* \*